United States Patent [19]
Sova et al.

[11] Patent Number: 5,263,922
[45] Date of Patent: Nov. 23, 1993

[54] VALVED BANDAGE

[75] Inventors: David Sova, Caledonia, Mich.; Melvin I. Eisenberg, Gurnee, Ill.

[73] Assignee: Plasco, Inc., Gurnee, Ill.

[21] Appl. No.: 749,996

[22] Filed: Aug. 26, 1991

[51] Int. Cl.$^5$ .................. A61F 13/00; A61F 15/00; A61L 15/00
[52] U.S. Cl. ........................... 602/59; 602/58; 602/47; 604/305; 128/203.11; 128/888
[58] Field of Search ............... 128/887, 888, 203.11, 128/202.28; 602/47, 53, 58, 59; 604/9, 34, 289, 305, 323, 326, 335; 623/2

[56] References Cited

U.S. PATENT DOCUMENTS

| | | | |
|---|---|---|---|
| 3,486,504 | 12/1969 | Austin, Jr. | 604/289 |
| 3,874,387 | 4/1975 | Barbieri | 128/888 |
| 4,795,449 | 1/1989 | Schneider et al. | 604/326 |
| 4,819,628 | 4/1989 | Eisenberg et al. | 128/203.11 |
| 4,946,451 | 8/1990 | Cianci | 604/335 |
| 5,056,510 | 10/1991 | Gilman | 602/59 |
| 5,086,763 | 2/1992 | Hathman | 128/888 |
| 5,090,406 | 2/1992 | Gilman | 602/47 |

FOREIGN PATENT DOCUMENTS 8800816 2/1988 PCT Int'l Appl. .................. 604/335

*Primary Examiner*—David Isabella
*Assistant Examiner*—Paul Prebilic
*Attorney, Agent, or Firm*—Jerome Goldberg

[57] ABSTRACT

A valved bandage and method for covering an open wound in the chest cavity. The bandage includes a flexible sheet having a hole formed therein. A normally closed one way valve section extends outward from the outside of the sheet and in communication with the hole. The bandage is secured over the chest wound, so that the valve is in alignment with the chest wound opening to close the chest wound. The bandage enables fluids from inside the chest cavity to flow into the valve, to open the valve and be released to the outside. The valve automatically closes after the flow of fluids into the valve substantially ceases, to prevent back flow of air from the outside to the inside of the chest cavity. The one way valve section of the bandage may be formed into an angled configuration, so that the position of the outlet of the angled valve section may be varied to provide optimum drainage of fluids.

4 Claims, 2 Drawing Sheets

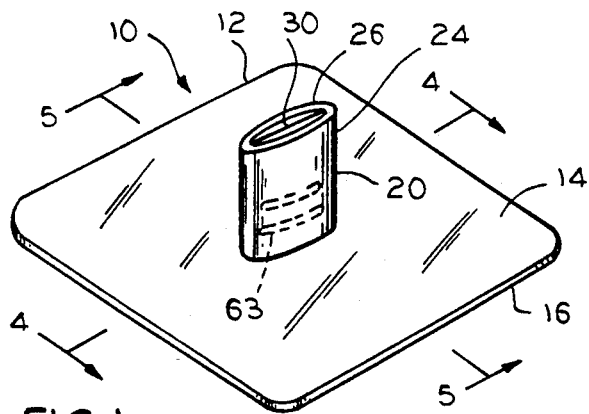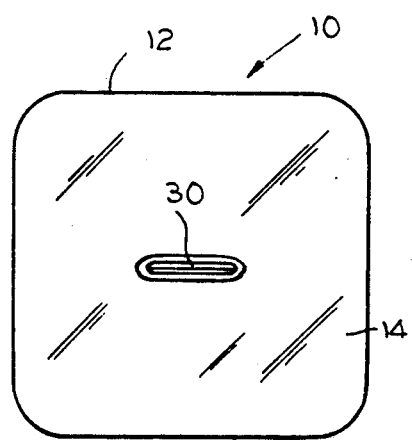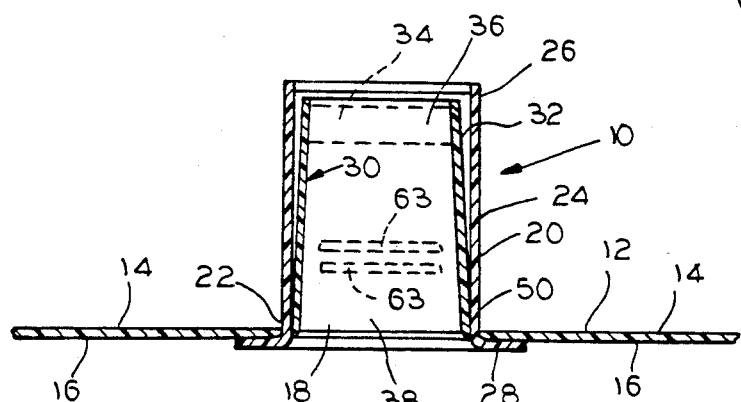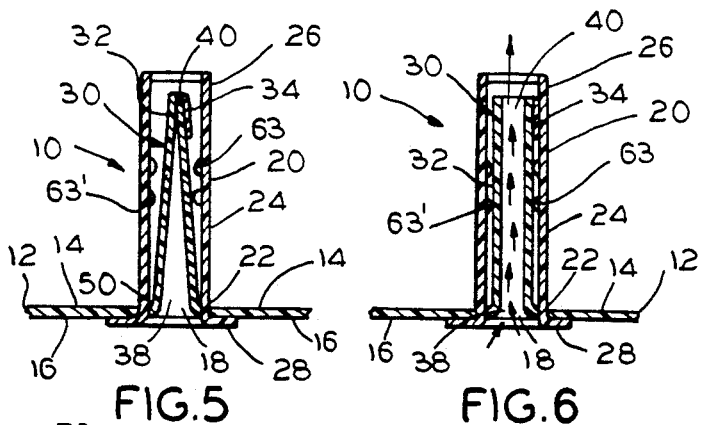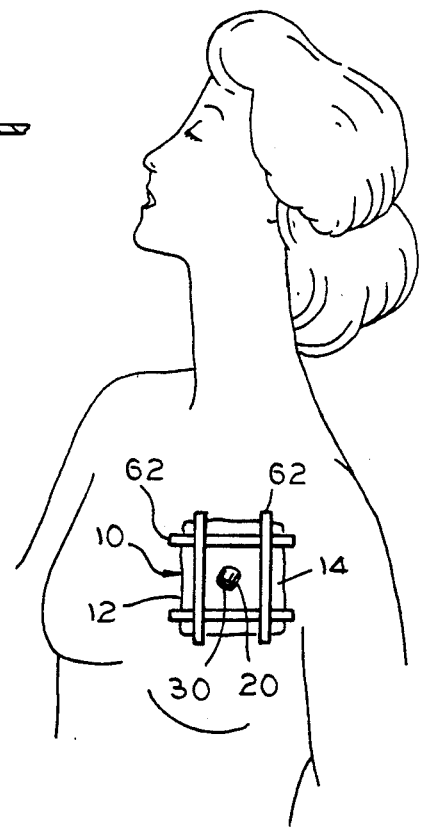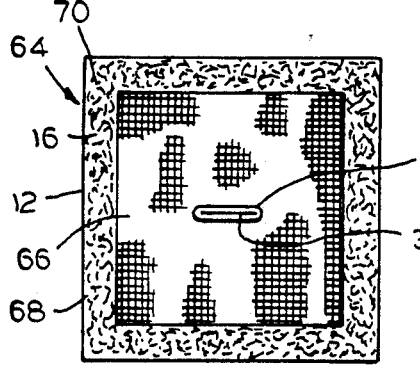

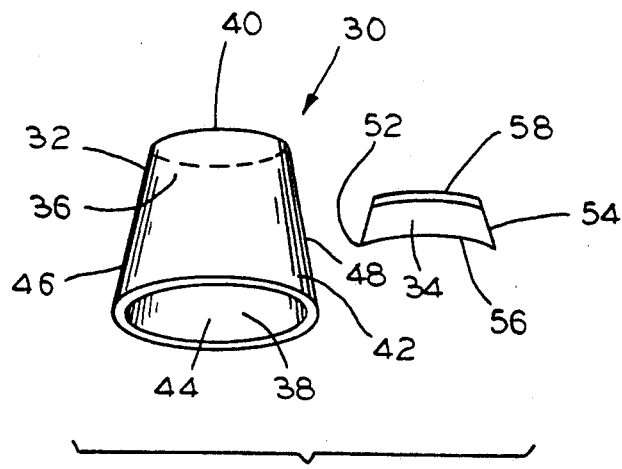 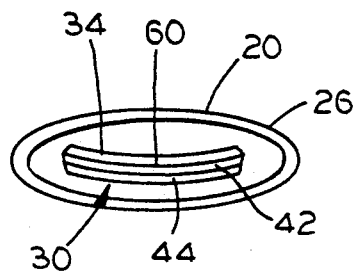
FIG. 8   FIG. 9
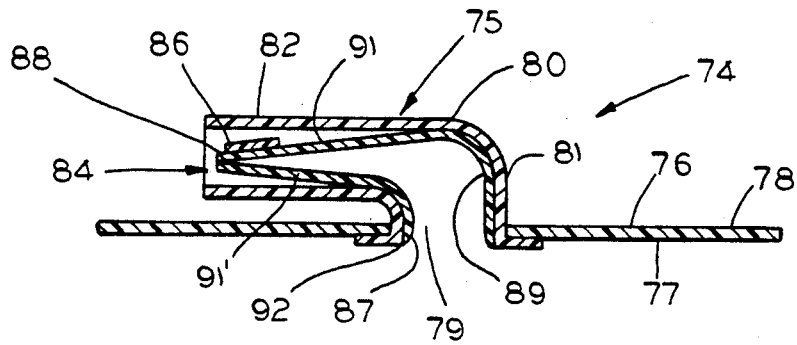
FIG. 10
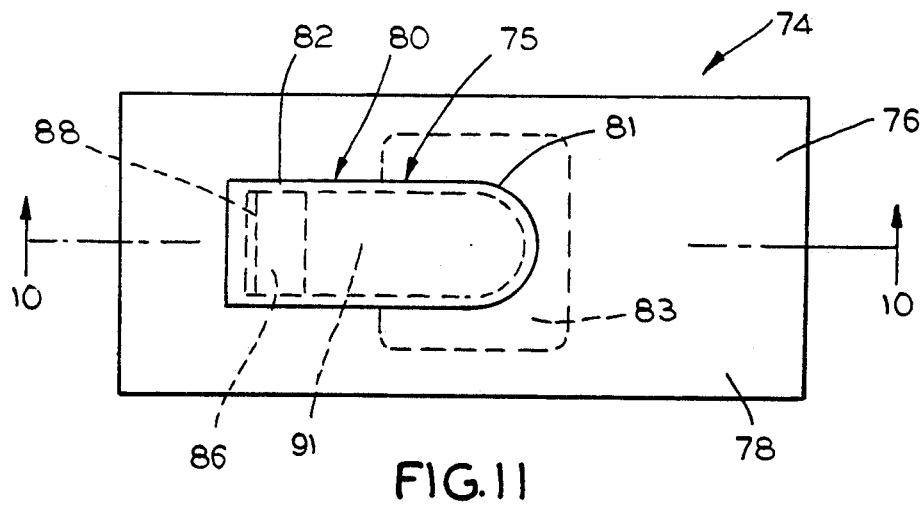
FIG. 11
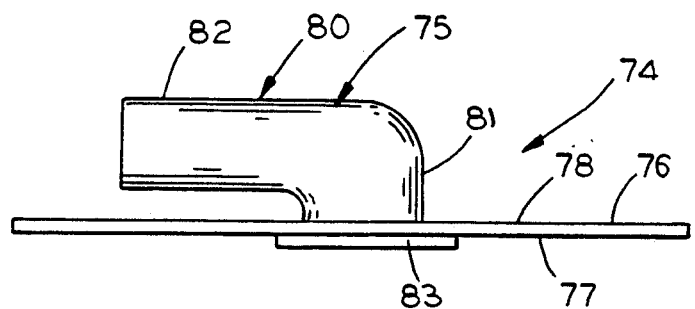
FIG. 12

VALVED BANDAGE

BACKGROUND OF THE INVENTION

This invention relates generally to a bandage for a chest wound and more specifically relates to a bandage device and method for covering an open chest wound.

Normally, when the chest expands and the diaphragm contracts, a negative pressure is developed inside the chest cavity. Air then rushes into the chest cavity from the upper airways and the trachea and expands the lungs. When the diaphragm and chest relax, a positive pressure is developed inside the lungs that force the air out from the lungs, through the trachea and discharged to the outside via the upper airways.

If a victim is wounded in the chest from a knife or bullet, causing a substantial opening in the chest cavity which is large enough to remain open, air will enter and exit the chest cavity through the wound opening in response to changes in the thoracic pressure. The air entering the thoracic cavity through the wound will only flow within the pleural space and will not enter the lungs, thereby eventually causing the chest to suck inward and the lungs to collapse.

If the wound opening is larger than the glottic or trachea opening, more air will enter the pleural space from the outside than will flow into the lungs from the upper airways. Thus, more air accumulates in the pleural space than within the lung parenchyma. Eventually this leads to hypoxia of the lungs, due to decreased exposure of lung tissue to oxygen.

Moreover, if the chest wound includes a flap, the air may become trapped, creating a tension force in the thorax which inhibits air inspiration into the lungs. The effect of this also causes hypoxia of the lungs.

Therefore, the air flow into the pleural space from the wound opening incapacitates the diaphragm so that it is unable to form a negative pressure to ventilate the lungs, and the wounded person will smother in the same manner as if the airways into the lungs were obstructed (but in this instance the airways into the lungs could be perfectly clear and unobstructed).

To treat the open wound leading into the pleural space and prevent the chest from sucking inward, the wound should be covered to close the chest opening from air flowing into the chest cavity. Prior to the invention herein, Saran wrap (a trademark to identify a thin plastic membraneous sheet material used to cover foods) having the property of clinging to materials, was suggested to be used to cover and close the open chest wound. Also a gel defibrillator pad or petroleum or VASELINE (Vaseline is a registered trademark identifying a product sold by Chesebrough Ponds Inc.) gauze were recommended to be used to cover the open wound and prevent pneumothorax from occurring. However, these procedures did not provide an exit path for discharging fluids from inside the chest cavity to the outside.

For a small opening chest wound, it was also suggested that the open end of a condom could be taped over the wound and the closed tip of the condom cut off to permit exiting of air from inside the chest cavity. For a larger opening chest wound, a plastic or rubber glove could be used to cover the wound opening and cutting off a tip from one of the fingers to provide an air exit.

The problems with the foregoing proposed solutions were that the opening made in the condom or the glove finger may be too large and cause substantial back flow of air into the chest cavity and prevent ventilation of the lungs; or that such opening may be too small and prevent sufficient discharge of the air or liquid pressure being built up in th chest cavity.

In U.S. Pat. No. 4,541,426 WEBSTER (1985), a dressing is disclosed for application over lesions of the skin, including a first layer formed of material which swells in contact with liquid and a second layer which does not swell or swells less than the first layer when in contact with liquid. Slits shaped apertures are formed in the layers and normally are closed when dry and open when liquid flows into the layers. The WEBSTER dressing appears to be usable for closing a chest wound, but it doesn't provide an opening for air to flow to the outside for removing the pressure on the lungs.

Therefore, a primary object of this invention is to provide a chest bandage and method to close an open chest wound and to release the fluids accumulated inside the chest cavity to the outside.

Another object is to provide a bandage for covering an open chest wound and inhibiting air flow through the wound opening from the outside but providing an exit pathway through the wound opening for discharging air or liquid from inside the chest cavity to the outside.

A primary feature of this invention is to provide a bandage having a normally closed valve for closing an open chest wound, and the valve opens in response to the force from air or liquid flowing into the valve from inside the chest cavity, for releasing such air or liquid to the outside. A further feature is that the valve automatically closes when the air or liquid flow or pressure into the valve from inside the chest cavity is substantially reduced or ceases.

A further feature is to provide a bandage having a valved section formed into an angled configuration to provide optimum drainage of fluids from inside the chest cavity to the outside.

SUMMARY OF INVENTION

The chest bandage and method of this invention are used to close an open chest wound of a victim, which may have been caused by a knife or bullet entering the chest cavity, and also to provide a discharge path for air or liquid inside the chest cavity to the outside.

The chest bandage comprises a flexible and pliable sheet having a central hole formed therein. A self closing one way valve section is secured to the sheet in communication with the sheet hole, for closing the open chest wound when the bandage covers the open chest wound.

The valve section may include a flexible sleeve having an inlet end in communication with the hole and an outlet end extending outward from the outer side of the sheet. A spring strip is attached to the sleeve adjacent to the outlet end for resiliently closing the outlet end. The flow of air or liquid into the sleeve from inside the chest cavity overcomes the resilient force of the spring strip to open the valve for enabling such air or liquid to exit to the outside. The flexible sleeve and spring strip may be enclosed in a hollow tube attached to the sheet to provide a protective shield.

The valve section may be formed into an angled configuration so that the position of the outlet from the valve may be varied, to provide optimum drainage of the fluids from inside the chest cavity to the outside.

In operation, the bandage is positioned over the open wound in the chest and attached to the victim with a suitable adhesive, so that the hole in the sheet is in alignment with the chest wound opening; a one way valve is secured to the sheet for normally closing the sheet hole and the open chest wound when the bandage is positioned over the chest wound; the valve opens from its normally closed condition in response to air or liquid flowing into the valve from inside te chest cavity, to provide a discharge path to the outside; and the valve resiliently closing after said air or liquid substantially ceases to flow into the valve or the fluid pressure has appreciably been reduced, to prevent back flow of air into the chest cavity.

The bandage may be secured to the chest with strips of adhesive tape. Alternatively, an adhesive substance may be applied around the border of the inner side of the sheet on the inner side thereof, and covered with a suitable covering material.

BRIEF DESCRIPTION OF DRAWINGS

Referring to the drawings in which the same characters of reference are employed to indicate corresponding similar parts throughout the several Figures of the drawing:

FIG. 1 is a perspective outer view of the valved chest bandage, embodying the principles of the invention;

FIG. 2 is a top view of the valved chest bandage in FIG. 1;

FIG. 3 illustrates the chest bandage taped to the chest of the victim to cover the open chest wound;

FIG. 4 is a fragmentary sectional view of the bandage, taken on the plane of the line 4—4 in FIG. 1, viewed in the direction indicated, and showing the one way valve inside the tubular enclosure;

FIG. 5 is a fragmentary sectional view, taken on the plane of the line 5—5 in FIG. 1, viewed in the direction indicated and showing the one way valve in a normally closed condition;

FIG. 6 is a similar fragmentary sectional view as Figure 5, and showing the valve in an open condition;

FIG. 7 is a bottom view of another embodiment of the valved chest bandage, having a liquid absorbent layer of material and an adhesive border on the inner side of the bandage;

FIG. 8 is a perspective view illustrating the parts of the valve including a sleeve and a spring strip prior to attachment at the outer end of the sleeve;

FIG. 9 is a top view of the one way valve and illustrating the valve in a closed condition;

FIG. 10 illustrates another embodiment of the invention and showing a cross sectional side view of the valved bandage having an angled valve section, taken on the plane of the line 10—10, and viewed in the direction indicated;

FIG. 11 is a top view of the angled valved bandage; and

FIG. 12 is a side view of the angled valved bandage.

DESCRIPTION OF PREFERRED EMBODIMENT

Referring now to FIGS. 1 thru 6, 8 and 9 of the drawings, the reference numeral 10 indicates generally a valved bandage for a chest wound penetrating the thorax cavity. The bandage 10 permits air and/or fluids to exit from the thorax cavity to the outside but prevents air from flowing into the thorax cavity from the outside.

The bandage 10 includes a flexible and pliable sheet 12 having an outer side or surface 14 and an inner side or surface 16. The sheet 12 includes a central oval hole 18 formed therein. The sheet 10 is shown having a square shape, but various other configurations would be suitable. The sheet 12 is a flexible and transparent material, impermeable to air and fluids, and may conform to the contour of the body area around the open chest wound. The sheet 12 is constructed from a flexible plastic material, which may be a polyvinyl chloride (PC) or similar material such as film forming thermoplastics including nylon, polyethylene, polypropylene, polyvinyl acetate, soft cellulous acetate etc.

A hollow, oval and rigid plastic tube 20 extends upward or outward from the outer surface 14 of the sheet 12, as may be seen from FIGS. 1,4,5, and 6. The tube 20 includes an inner end 22, a body portion 24 and an outer end 26. The cross-sectional area of the tube body portion 24 is just slightly less than the area of the hole 18, and, hence, the tube 20 is snugly received or press fits in the hole 18 and extends outward from the outer surface 14 of the sheet.

The tube 20 includes an oval lip 28 which extends around the inner end 22 of the tube 16 and is integrally formed thereto. The lip 28 is heat fused to the inner surface 16 of the sheet 12 adjacent to the hole 18 to circumscribe the hole 18, and the body portion 24 of the tube 20 passes through hole 18, to extend outward from the outer surface 14 of the sheet 12. The tube 20 is made from a semi-transparent, rigid, elastomeric material or other suitable material.

A one way, self closing valve indicated generally by the reference numeral 30 is positioned inside the tube 20. As may be seen from FIG. 4,5,6 and 8, the valve 30 comprises a sleeve 32 and an arcuate spring strip 34 which may have a normal arcuate shape. The valve 30 is positioned inside the tube 20 which functions as a protective shield for the more fragile constructed sleeve 32 and spring strip 34.

The sleeve 32 includes an inlet end 38 and an outlet end 40. Both ends 38,40 of the sleeve 32 are open. The spring strip 34 is attached to the outlet end 40 of the sleeve 32. The outlet end 40 is normally maintained closed by the closing resilient force of the spring strip 34.

The sleeve 32 may be constructed from two substantially identical confronting thin, flexible walls 42,44 which are heat sealed along the opposite longitudinal edges 46,48 thereof (FIG. 8). The transverse or horizontal dimensions of the walls 42,44 progressively decrease and the marginal edges 46,48 taper inward from the inlet end 38 to the outlet end 40. The material for the walls 42,44 may be a suitable plastic such as a polyvinyle chloride sheet material.

The sleeve 32 is inserted inside the tube 20 and the inlet end 38 of the sleeve 32 is opened so that the walls 42,44 are spread apart and the inlet end 38 is heat sealed to the oval inside surface 50 of the tube 20. Therefore, the inlet end 38 is always open. When the tube 20 is fused to sheet 12, the inlet end 38 of the sleeve 32 is aligned with the hole 18 in the sheet 12. Hence, any fluids flowing out from the chest wound opening would flow into the inlet end 38 for discharge through the outlet end 40 of the one way valve 30.

The arcuate spring strip 34 (FIG. 8) is rigid and flexible and may be constructed from a polyvinyle chloride or similar material. The spring strip 34 extends across the wall 42 at the outlet end 40 of the sleeve 32. The side edges 52,54 of the spring strip 34 are heat sealed to the marginal edges 46,48 of the walls 42,44 of the sleeve 32.

Similar to the construction of the walls 42,43, the spring strip 34 tapers inward from the inner transverse edge 56 to the outer transverse edge 58.

The spring strip 34 has a convex inner side 60. Normally, the spring strip 34 resiliently forces the adjacent portions of the sleeve walls 42,44 into taut contact with the inner side 60, as may be seen in FIG. 9 to provide a sufficiently tight closure between the walls 42,44 at the outlet end 40 of the sleeve 32 to prevent back flow of air from the outside to the inside of the chest cavity.

Strips of conventional adhesive tape 62 or other suitable adhesive may be used to secure the bandage 10 on the victim and over the open chest wound, as shown in FIG. 3.

A pair of spaced apart ribs 63 are integrally formed to the inside surface of tube 24, and another pair of ribs 63' are formed to the opposite inside surface of the tube. The ribs 63,63' prevent the sleeve 32 from sticking to the inside surfaces of the tube 24.

In operation, the inner side 16 of the sheet 12 is placed in an opposed relationship with the open wound so that the hole 18 communicates with the open wound and the closed valve 30 is in alignment with the open wound. Since the air impervious sheet 12 is flexible and pliable, it is forced to conform to the contour of the chest area around the open wound and secured in place with the strips of adhesive tape 62. The valved bandage 10 should now be air tight and prevent any back flowing of air into the thorax cavity from the outside. The flow of liquid or air from inside the thorax cavity and through the open wound has an exit passageway to the outside via the hole 18 in the sheet 12 and the valve 30. When there is sufficient pressure of air or liquid flowing into the valve 30 to overcome the resilient force of the spring strip 34, the valve 30 opens discharging the air or liquid to the outside. When the fluids flowing out from the open wound has substantially ceased, the valve 30 automatically closes, as the resilient force of the spring strip 34 moves the outlet end 40 of the sleeve 30 to the closed condition.

Turning now to FIG. 7, an alternative embodiment for a valved bandage indicated generally by the reference numeral 64, is shown. The valved bandage 64 has the same features as the valved bandage 10, but also includes a layer 66 of a liquid obsorbent material attached to the inner side 16 of the plastic sheet 12 and spaced from the perpheral edge. An adhesive substance 68 is spread along a peripheral border 70 on the inner side 16 of the sheet 12.

The layer 66 is compressible and may be constructed from a suitable gauze material. An oval aperture 72 is formed in the layer 66 in communication with the hole 18 of the sheet. When the bandage 64 is placed over the open chest wound, the aperture 72 in the layer 66 is aligned with the open wound and fluids seeping out from the wound are obsorbed by layer 66, although any sustained flow of fluids from the wound would be discharged through the valve 30.

The adhesive substance 68 along the border 70 may be covered with conventional protective strips of paper (not shown) having a wax like coating, which are pulled away from the adhesive 68 prior to utilizing the adhesive for securing the bandage 64 on the victim.

Referring now to FIGS. 10,11 and 12, a modified embodiment of a valved bandage indicated generally by the reference numeral 74 is shown and includes an angled valve section 75 secured to a sheet 76.

The sheet 76 is flexible and similarly constructed as the sheet 12 in FIG. 1. The sheet 76 includes an inner side 77, an outer side 78 and a hole 79 centrally formed therein.

The valve section 75 comprises a substantially right angular, hollow, and open ended pipe 80 having an inward leg 81 and an outward leg 82. The inward leg 81 of the pipe 80 is substantially perpendicular to the sheet 76 and may be attached to the sheet 76 in the same manner the tube 20 is attached to sheet 12. The pipe 80 may have an oval cross sectional area similar to the oval construction of the tube 20.

The pipe 80 may have an oval lip 83 which extends around the inner end 84 of the pipe 80 and is integrally formed thereto. The lip 83 is heat fused to the inner side 77 of the sheet 76 around the hole 79.

A one way, self closing valve indicated generally by the reference numeral 84 is positioned inside the pipe 80 which acts as a protective shield. The valve 84 includes an open ended sleeve 85 and a spring strip 86.

The sleeve 85 includes an inlet end 87 and an outlet end 88, and has a right angular, oval shape to conform to the inside of the pipe 80. As shown in FIG. 10, an elbow 89 is formed in the sleeve 85 similar to the bend 90 on the inside of the pipe 75.

The sleeve 85 may be constructed from two substantially identical confronting thin, flexible walls 91,91' and sealed together along the longitudinal edges thereof.

The sleeve inlet end 87 is attached to the inside of the open inner end 92 of the pipe 80 to maintain the inlet end 87 widely open. The spring strip 86 is attached to the sleeve wall 91 at the outlet end 88 of the sleeve 85 to maintain the outlet end 88 normally closed. The outlet end 88 moves from a closed condition to an open condition, in response to the flow of air and liquid from inside the thorax and into the sleeve 85 via the open chest wound.

When a victim is severly wounded from a body penetrating weapon or missle causing an opening in the chest, it is extremely important for the paramedic, doctor, nurse or other emergency trained person to immediately close off any air flow into the chest cavity from the wound opening which would impede and prevent vital lung action. Each of the valved bandages 10, 64 and 74 of the invention herein closes the open chest wound to prevent air from flowing from the outside and into the thorax cavity via the open chest wound; and switches to an open condition for discharging fluids from inside the thorax and through the open chest wound to the outside; and then switches to the closed condition when the pressure from fluids flowing into the bandage valve has substantially decreased. Thus, fluids including air and/or liquid accumulating inside the thorax cavity are discharged to the outside without air back flowing through the open chest wound and into the thorax cavity.

Various modifications of the invention of a valved bandage and method for closing a chest wound described herein, are within the spirit and scope of the invention, the scope of which is limited solely and defined by the appended claims.

We claim:

1. A bandage for covering an open chest wound in the body of a victim comprising:

a sheet of material having a hole formed therein, said sheet including an outer side and an inner side, said sheet being flexible for conforming to the contour of the area of the chest adjacent the open wound;

a sleeve for positioning at the outer side of said sheet, said sleeve having an inlet end and an outlet end, said inlet end of the sleeve being in communication with said hole so that fluid from the open chest wound flows into said inlet end and through said sleeve to the outlet end;

a hollow rigid tube secured to said sheet and extending outward from the outer side of the sheet, said tube enclosing said sleeve to provide a protective shield for the sleeve;

an adhesive substance positioned along the peripheral border on the inner side of the sheet for operatively securing said sheet over the open wound so that the inner side of said sheet is opposed to said wound and said hole in the sheet is in alignment with the open wound;

a layer of material secured to the inner side of the sheet for absorbing liquid from the open wound, said layer of material being positioned inside from said peripheral border of said adhesive substance, said layer of material having an aperture therein in communication with said hole in the sheet; and a spring strip secured to said outlet end of the sleeve for resiliently closing said outlet end, said outlet end of the sleeve opening in response to said fluids flowing into the sleeve from the open wound and overcoming said resilient force of the spring strip, said spring strip resiliently closing said outlet end when said fluid from the open wound has substantially ceased flowing.

2. A chest bandage for covering an open wound of a victim comprising:

a sheet of material having a hole formed therein, said sheet including an outer side and an inner side;

a hollow tubular means secured to the sheet and aligned with the hole, the tubular means including an inlet end and an outlet end, said inlet end being in communication with said the hole so that fluid from the open wound flows into said tubular means;

a one way valve associated with the outlet end of the tubular means to permit said fluid to flow from inside the tubular means to the outside of the body and to prevent back flow of fluid into said tubular means from the outside of the body;

said tubular means being formed into an angular configuration for varying the position of the valve to vary the location of the fluid discharge from the valve in response to a change of position of said sheet; and attaching means for operatively securing said sheet over the open wound, so that the inner side of said sheet is opposed to the open wound.

3. A bandage for covering an open wound of a victim comprising:

a sheet of material having a hole formed therein, said sheet including an outer side and an inner side;

an open ended hollow pipe having an angular configuration, said pipe including an inward leg and an outward leg, said inward leg extending outward from the outer side of the sheet, an inner end of the inward leg being attached to the sheet adjacent said hole so that the inside of said pipe is aligned with the hole;

said outward leg angularly formed to the inward leg and spaced from the sheet;

a sleeve positioned inside said pipe and including an inlet end and an outlet end, said sleeve having an angular configuration to conform to the inside of the pipe, said inlet end of the sleeve being in communication with said hole so that fluid from the open wound flows into said inlet end and through said sleeve to the outlet end;

a one way valve associated with the outlet end of the sleeve to permit said fluid to flow from inside the sleeve to the outside of the body and to prevent fluid flow into said sleeve from the outside of the body; and attaching means for operatively securing said sheet over the open wound, so that the inner side of said sheet is opposed to said wound and said hole in the sheet is in alignment with the open wound.

4. The bandage of claim 3, wherein said inward leg of the pipe is substantially perpendicular to the sheet and said outward leg is substantially perpendicular to the inward leg, the inside of the pipe having a substantially right angular pathway, said sleeve having a substantially right angular shape to conform to said pathway inside the pipe.

* * * * *